United States Patent
Bayer et al.

(10) Patent No.: US 9,394,612 B2
(45) Date of Patent: Jul. 19, 2016

(54) IMPLANT AND METHOD FOR MANUFACTURING SAME

(75) Inventors: Ullrich Bayer, Admannshagen-Bargeshagen (DE); Bjoern Klocke, Zurich (CH)

(73) Assignee: BIOTRONIK VI PATENT AG, Baar (CH)

( * ) Notice: Subject to any disclaimer, the term of this patent is extended or adjusted under 35 U.S.C. 154(b) by 496 days.

(21) Appl. No.: 12/786,775

(22) Filed: May 25, 2010

(65) Prior Publication Data

US 2010/0324654 A1 Dec. 23, 2010

Related U.S. Application Data

(60) Provisional application No. 61/219,401, filed on Jun. 23, 2009.

(51) Int. Cl.
*B05D 3/14* (2006.01)
*A61F 2/82* (2013.01)
*A61F 2/06* (2013.01)
*C23C 14/34* (2006.01)
*C23C 24/04* (2006.01)
*A61L 31/02* (2006.01)
*A61L 31/14* (2006.01)
*C23C 26/00* (2006.01)

(52) U.S. Cl.
CPC ............... *C23C 24/04* (2013.01); *A61L 31/022* (2013.01); *A61L 31/148* (2013.01); *C23C 26/00* (2013.01); *A61L 2400/18* (2013.01)

(58) Field of Classification Search
CPC .............. C23C 14/34; A61F 2/82; A61F 2/06
USPC ........................... 427/460, 471, 481, 447, 448
See application file for complete search history.

(56) References Cited

U.S. PATENT DOCUMENTS 4,163,153 A * 7/1979 Tamura ................... H01J 27/20 250/396 R
4,467,240 A * 8/1984 Futamoto .............. H01J 27/022 313/336

(Continued)

FOREIGN PATENT DOCUMENTS

EP 1 402 849 A1 4/2008
EP 2 206 526 A2 11/2009

(Continued)

OTHER PUBLICATIONS

Peuster et al., Long-term Biocompatibility of a corrodible peripheral iron stent in the porcine descending aorta, 2006, Biomaterials 27 (2006) 4955-4962.*

(Continued)

*Primary Examiner* — Dah-Wei D Yuan
*Assistant Examiner* — Hai Yan Zhang
(74) *Attorney, Agent, or Firm* — Wagenknecht IP Law Group PC

(57) ABSTRACT

The present invention relates to a method for manufacturing an implant, in particular an intraluminal endoprosthesis, with a body containing metallic material, preferably iron. The method includes the following steps to control degradation of the implant: (i) providing the body of the implant; and (ii) tribochemically treating at least part of the body surface by means of beam particles. An implant produced in this way is also described.

6 Claims, 2 Drawing Sheets

(56) References Cited

U.S. PATENT DOCUMENTS

| | | | | |
|---|---|---|---|---|
| 4,608,277 | A * | 8/1986 | Greiner et al. | 427/213.3 |
| 5,344,425 | A * | 9/1994 | Sawyer | 606/198 |
| 6,010,573 | A * | 1/2000 | Bowlin | 118/620 |
| 6,337,540 | B1 * | 1/2002 | Corbin | H01J 27/26 204/298.41 |
| 6,861,088 | B2 * | 3/2005 | Weber et al. | 427/2.24 |
| 7,247,338 | B2 * | 7/2007 | Pui | A61L 31/16 427/2.24 |
| 2003/0149471 | A1 * | 8/2003 | Briana et al. | 623/1.13 |
| 2004/0158330 | A1 * | 8/2004 | Muller et al. | 623/23.57 |
| 2006/0229711 | A1 * | 10/2006 | Yan | A61F 2/02 623/1.38 |
| 2007/0187061 | A1 * | 8/2007 | Siddle | B22D 17/2023 164/312 |
| 2008/0248086 | A1 * | 10/2008 | Asgari | A61L 27/446 424/426 |
| 2008/0249638 | A1 * | 10/2008 | Asgari | A61F 2/28 623/23.75 |
| 2009/0118815 | A1 * | 5/2009 | Arcand et al. | 623/1.15 |
| 2010/0057196 | A1 * | 3/2010 | Pathak | 623/1.42 |
| 2010/0292701 | A1 * | 11/2010 | Fisher | A61B 17/14 606/82 |

FOREIGN PATENT DOCUMENTS

| | | |
|---|---|---|
| FR | 2 775 919 A1 | 9/1999 |
| WO | WO 2008/034066 A1 | 3/2008 |
| WO | WO 2009/050251 A3 | 4/2009 |

OTHER PUBLICATIONS

European Search Report for Priority Document EP 10 15 7347.
Peuster et al., Long-term biocompatability of a corrodible peripheral iron stent in the porcine descending aorta, Biomaterials, 2006, 27:4955-4962.

* cited by examiner

IMPLANT AND METHOD FOR MANUFACTURING SAME

CROSS REFERENCE TO RELATED APPLICATIONS

This invention claims benefit of priority to U.S. provisional patent application Ser. No. 61/219,401, filed on Jun. 23, 2009; the contents of which is herein incorporated by reference in its entirety.

FIELD OF THE INVENTION

The present invention relates to a method for manufacturing an implant, in particular an intraluminal endoprosthesis, having a body containing metallic material, preferably iron, in particular an iron alloy, and a corresponding implant obtainable or obtained by such a method.

BACKGROUND OF THE INVENTION

A large number of medical endoprostheses or implants for a range of applications is known from the prior art. Endovascular prostheses or other endoprostheses, for example stents, fasteners for bones, for example screws, plates or nails, surgical suture material, intestinal clamps, vessel clips, prostheses in the area of hard and soft tissue, and anchoring elements for electrodes, in particular pacemakers or defibrillators are understood as implants in terms of the present invention.

Stents used for treating stenoses (vessel constrictions) are used these days particularly frequently as implants. They have a body in the form of a punctured tubular or hollow-cylindrical grating, where required, open at both longitudinal ends. The tubular grating of such an endoprosthesis is inserted into the vessel to be treated and serves to support the vessel. Stents have proven themselves in particular for treatment of vessel diseases. Through the use of stents constricted regions in vessels can be widened, resulting in a gain in lumen. Using stents or other implants produces an optimal vessel cross-section primarily necessary for successful therapy, although the ongoing presence of this type of foreign body launches a cascade of microbiological processes which can result in a gradual increase in the stent and in the worst case scenario in vessel obstruction. An approach to solving this problem is to make the stent or other implants from a biodegradable material.

Biodegradation is understood to mean hydrolytic, enzymatic and other decomposition processes determined by metabolism in the living organism, caused especially by bodily fluids coming into contact with the biodegradable material of the implant and leading to gradual dissolution of the structures of the implant containing the biodegradable material. At a certain point the implant loses its mechanical integrity through this process. The term biocorrosion is used frequently, similarly to the term biodegradation. The term bioresorption includes subsequent resorption of the waste products through the living organism.

Materials suitable for the body of biodegradable implants can for example contain polymers or metals. The body can comprise several of these materials. A common characteristic of these materials is their biodegradability. Examples of suitable polymer compounds are polymers from the group cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxy butyric acid (PHB), polyhydroxy valerian acid (PHV), polyalkyl carbonates, polyorthoesters, polyethylene terephthalate (PET), polymalonic acid (PML), polyanhydrides, polyphosphazenes, polyamino acids and their copolymers and hyaluronic acid. Depending on the preferred properties polymers can be present in pure form, in derivatized form, in the form of blends or as copolymers. Metallic biodegradable materials are based predominantly on alloys of magnesium and iron. The present invention preferably relates to implants the biodegradable material of which at least partially contains a metal, preferably iron, manganese, zinc and/or wolfram, in particular an iron-based alloy (hereinafter abbreviated as iron alloy).

In making biodegradable implants the attempt is made to control the degradability according to the intended therapy or application of the respective implant (coronary, intracranial, renal etc.). It is for example an important target range for many therapeutic applications that the implant loses its integrity in a period of four weeks to six months. In this case, integrity, that is mechanical integrity, is understood as the property, wherein the implant barely has mechanical losses relative to the undegraded implant. This means that the implant is still sufficiently mechanically stable that at the most the pressure has fallen for example only slightly to 80% of the nominal value. The implant can thus still comply with its chief function, keeping the vessel open, when integrity is present. Alternatively, the integrity can be defined by the implant being so mechanically stable that it has barely undergone geometric changes in its loaded state in the vessel, for example it does not noticeably slump, that is has at least 80% of the dilation to diameter under load, or in the case of a stent has barely begun supportive aspirations.

Implants with an iron alloy, in particular stents containing iron, are particularly cost-effective and easy to manufacture. For example, for treating stenoses these implants tend to lose their mechanical integrity or supportive effect after a comparatively long period, that is, only after a dwell time in the treated organism of ca. 2 years. This means that the collapse pressure in implants containing iron is reduced too slowly for this application over time. For other applications of implants containing iron, for example in orthopedics, the degradation period is short, however.

Various mechanisms of degradation control of implants are already described in the prior art. These are based for example on inorganic and organic protective layers or their combination, which set resistance against the human corrosion medium and the corrosion procedures running. Solutions known to date are distinguished by focusing on barrier layer effects based on spatial and the most defect-free separation of the corrosion medium from the metallic material. These result in the degradation time being prolonged. In this way the degradation protection is safeguarded by variously composed protective layers and by defined geometric distances (diffusion barriers) between the corrosion medium and the basic magnesium material. Other solutions are based on alloy constituents of the biodegradable material of the implant body, which influence the corrosion process through a shift of position in the electrochemical series. Further solutions in the area of controlled degradation cause break-off effects from application of physical (for example local modifications in cross-section) and/or chemical changes in the stent surface (for example locally and chemically variously composed multilayers). With the above solutions, however, there is mostly no success in placing the dissolution occurring via the degradation process and the resulting cell breaks in the stipulated time window. The consequence is variability of the degradation of the implant, which is begun either too soon or too late or excessive.

A further problem in connection with coatings also results from stents or other implants usually taking on two states, specifically a compressed state with a small diameter and an expanded state with a larger diameter. In the compressed state the implant can be introduced into the vessel to be supported by means of a catheter and positioned at the site to be treated. At the treatment site the implant is then dilated for example by means of a balloon catheter or transitions to the expanded state (with use of a shape memory alloy as implant material) for example by being heated to above a transition temperature. Due to this change in diameter the body of the implant is subjected to mechanical stress. Other mechanical stresses of the implant can occur during manufacture or with movement of the implant in or with the vessel, into which the implant is inserted. The drawback to the abovementioned coatings is that the coating of the implant tears during deformation (for example due to microtears developing) or is also partially removed, causing unspecified local degradation. Also, insertion and rate of degradation depend on the size and distribution of the microtears resulting from deformation, which cannot be controlled well as imperfections, leading to substantial scattering in degradation times.

SUMMARY OF THE INVENTION

As a result, the object of the present invention is to provide a method for producing an implant which has a metallic material in particular and causes degradation of the implant in the desired target range, in particular in a shorter period. At the same time the degradation is supposed to take place at a controllable point in time and additionally enable dilation or deformation of the implant without appreciable influence on the degradation performance. The object of the invention is accordingly to create such an implant.

The above task is solved by a method including the following steps: (i) providing the body of the implant; and (ii) tribochemically treating at least part of the body surface by means of beam particles.

The tribochemical treatment is mechanical and if needed chemical surface treatment by means of bombardment or radiation of the treated part of the body surface by beam particles (particles) or by treatment using milled or abrasive particles in grinding drums or ball mills. The method is also designated as particle beaming. The beam, milled or abrasive particles are here particles comprising one or more materials with an average particle size in the nano or micrometer range. The particle size is hereby determined under application of a scanning electron microscope (for particle sizes smaller than or equal to 3 µm) or a light microscope (for particle sizes greater than 3 µm). The electron or light-microscopic recordings are gauged and the average particle size is determined from the measured values, for example by averaging (arithmetic means). The beam particles accordingly comprise not individual atoms, ions or compounds, but in each case comprise a group or a structure of atoms, ions or molecular compounds. Tribochemical treatment is generally performed at room temperature, that is, in the cold state. Hereinbelow reference is mainly made to radiating by means of beam particles as tribochemical treatment method. The executions for this however apply similarly also for milling and grinding processes in grinding drums and ball mills.

Tribochemical treatment of at least part of the body surface particularly easily and cost-effectively generates surface roughness and/or coating in each case on the treated part of the body surface by means of the beam particles. With respect to its chemical composition, degree of hardness and/or surface morphology the originally present surface is modified purposefully, causing a change to the degradation performance of the treated implant. The changes to the surface occurring from tribochemical treatment depend in particular on the type, size, form and chemical composition of the beam particles, on the beam pressure and the distance between the jet nozzle and the implant body and the material of the implant body. Tribochemical treatment of the body surface also eliminates surface contamination and causes edge-rounding. Details on the mechanical and/or chemical changes of the surface and the resulting particular characteristics of the degradation performance are specified in conjunction with the embodiments of the inventive method discussed hereinbelow.

Overall, tribochemical surface treatment has available a large number of operational parameters determining later surface properties. These relate to both the properties of the radiated material and the beam parameters as well as subsequent processing methods which can be carried out optionally.

An added advantage of the inventive method is that with tribochemical treatment of the implant, subsequent electropolishing otherwise used in manufacturing implants is often unnecessary and especially must inevitably be omitted. Subsequent electropolishing would remove part of the applied coating and/or the surface morphology caused by tribochemical treatment and thus the degradation performance are changed. Optionally, electropolishing can be completed prior to tribochemical treatment of the implant to produce additional edge-rounding of the implant.

In the present invention the body of the implant comprises at least part of the implant, preferably the majority of the implant, which brings about the mechanical integrity of the implant.

In a preferred embodiment the beam particles used for tribochemical treatment have at least one inert hard material, preferably a compound from the group containing oxides, in particular $Al_2O_3$, $SiO_2$, $ZrO_2$, carbides, in particular TiC, SiC, $B_4C$, $Be_2C$, oxicarbides, nitride, in particular TiN, cubic boron nitride (c-BN, β-BN, "Borazon"), $Si_3N_4$, AlN and TiAlN, carbonitride, natural or synthetic diamond and boron. These materials exhibit sufficient hardness to create with them mechanical changes in the surface of the implant, resulting in acceleration of degradation. The mechanical changes in the surface of the tribochemical treated part of the implant or in the near-surface volumes are described hereinbelow.

In a further embodiment the beam particle can comprise electrically conductive material. For example, a compound or an element of the group TiN, TiC, TiCN, metallic elements and their alloys can be used as electrically conductive (conductive) material. When they stick to the surface of the implant body or penetrate a near-surface volume of the implant body, these beam particles additionally cause a corrosion effect based on local element development. In a particularly preferred embodiment hard granulate of a CuZn alloy can be used. Part of the CuZn beam particles used in treatment adheres to the surface and later has a particularly corrosion-accelerating effect.

A further advantage of using electrically conductive particles is the following: there is the possibility of electrically charging the electrically conductive (conductive) beam particles in a chamber nozzle and inversely poling the implant corresponding to the chamber nozzle (for example by applying a sinusoidal alternating voltage). In the resulting electrical field the electrically loaded beam particles are accelerated to the opposite pole (implant body) where they impact with a certain, high kinetic energy. This can be varied by the parameters of the electrical alternating field (potentially high, frequency). The mechanical "impact", that is the kinetic energy transferred to the body surface and the resulting mechanical changes of the body surface or the near-surface volumes of the body, can be controlled by the properties of the electrical alternating field in addition to the parameters of size and form (sharp-edged or rounded) of the beam particles.

Electrically conductive beam particles of metallic material or electrically conductive hard materials (for example TiN) can also be used exclusively together with metal beam particles basically for the tribochemical treatment suggested above. There is also the possibility of using a combination of electrically conductive and electrically non-conductive particles in a modified tribochemical processing facility.

Tribochemical treatment results in roughening of the surface of the implant body and mechanical surface stabilizing effects in the near-surface structural area of the implant body via local cold deformation with use of extremely hard beam particles containing oxide, carbide, nitride or oxicarbide, beam particles of electrically conductive materials, which impact the implant body with high kinetic energy, as well as beam particles of other abovementioned materials or mixtures thereof. These changes to the surface cause a rise in the crystallographic imperfection density, in turn causing a drop in corrosion resistance of the affected areas of the implant body.

Due to the mechanical effect of the inert hard particles (where required including the electrically conductive beam particles, if they have comparable hardness) on the surface of the implant body, channels of preferably approximately 2 μm to approximately 5 μm deep and approximately 2 μm to approximately 5 μm wide are formed, which can run mostly parallel to the direction of insertion, but also obliquely thereto. This surface structure is also described hereinbelow as a fissured structure.

The surface structure resulting from the inventive tribochemical treatment can be characterized summarily by means of following morphometric and chemical properties: microroughening in the roughness area Rz of several μm; submicroroughening (caverning) in the roughness area Rz of <1 μm; chemical modification via adhered conductive beam particles and/or salts; and a dislocation density increased in comparison to the basic material to a depth of the implant body volume of up to approximately 5 μm starting out from the body surface.

Micro-roughening occurs first and foremost from primary bombardment with relatively coarse hard material particles of high kinetic energy. These can be achieved both by the increased mass of the beam particles and by greater beam pressure. Also, the kinetic energy can also be varied by the electrical parameters of the above-described electrical alternating field with use of electrically conductive material for the beam particles. Submicro-roughening is generated by the use, described below, of small salt particles which adhere to the surface of the implant body and immediately initiate a corrosion procedure under moist environmental conditions.

Also, the fissured structure of the body surface can act as material reservoir for another coating described below by means of a pharmaceutically active substance, stored as nano- or microparticles and can for example include substances promoting bone growth, such as calcium phosphates, temporarily effective contrasting agents and/or cell growth-inhibiting (if needed also radioactive) substances. Glide agents can also be effectively embedded in the fissured structure to decrease the friction coefficients in a catheter.

In particular, a drop in the degradation duration is achieved in an embodiment of the inventive method, in which the beam particles used for tribochemical treatment have at least one salt, preferably a compound from the group containing NaCl, CaCl, $MgCl_2$, in particular dry-stored $MgCl_2$.

The beam particles with at least one salt are beamed at a certain preset pressure onto the surface of the implant. The pressure range to be used advantageously is between 0.5 and 5.0 bar. The processing duration is in the vicinity of 0.5 to 30 min. Applying pressure during beaming also causes, apart from roughening of the body surface, partial adhesion of the beamed salts and where required other beam particles on the body surface. In the process, the beam particles, which comprise the corrosively acting salts, can also be mixed with beam particles of inert hard material. The salts adhering to the surface of the implant body cause accelerated corrosion of the surface, wherein the corrosion also depends on the subsequent processing of the implant then performed on the tribochemical treatment.

In this embodiment exclusive use of corrosively effective salts as beam particles is also possible. In particular, dry-stored $MgCl_2$ is used as granular salt of defined granulation as beaming agent without addition of other abrasively acting hard substances. Dry-stored $MgCl_2$ should be used for the reason that there would otherwise be the danger of lumping due to strong hygroscopy of the materials.

Due to their minimal hardness $MgCl_2$ particles cause no substantial mechanical surface change, that is, no substantial surface roughening. However, a large proportion of the $MgCl_2$ particles adheres to the surface of the implant. Corrosion of the surface is first delayed during subsequent storage of the thus treated implant in an extremely dry atmosphere and under the exclusion of air. Only at the time of implantation and contact of the implant, for example a stent, with bodily fluid does the adhesive $MgCl_2$ strongly begin to work corrosively, resulting in accelerated degradation.

In the case of not exclusively dry storage the $MgCl_2$ particles remain temporarily until to dissolution in the tribochemically generated submicro-roughening, accelerate the corrosion in the presence of humidity and thus boost the dimensions of the submicro-roughening cavity.

In a further embodiment the beam particles used for tribochemical treatment comprise at least one compound from the group containing Mg, MgO and $Mg(OH)_2$, wherein the content of elementary magnesium in the total weight of the beam particles beamed during treatment of an implant is preferably comparatively low, in particular maximum 20% by weight. The remaining portion of the beam particles can comprise MgO and/or $Mg(OH)_2$. It should of course be noted that for reasons of fire prevention an inert gas environment should be used when working with pulverulent Mg.

Treatment with beam particles of the composition of this embodiment, preferably with a particle size (particle size) in the nanometer to micrometer range, leads to uniform coating of the body surface with the abovementioned beam particle material. The resulting surface coating with Mg, MgO and/or $Mg(OH)_2$ has a layer density of a few nanometers to approximately 2 μm, which leads to targeted adjustable biochemical reactions at the implantation site in contact with bodily fluid. The coating preferably has a gradient in its composition, wherein the content of beamed Mg, MgO and/or $Mg(OH)_2$ increases in the direction of the surface of the treated implant. The claimed biochemical reactions are for example a decrease in noontime development in implants or the local increase of the pH value during conversion of MgO to $Mg(OH)_2$, which has for example a favorable effect in drug release from a polymer covering layer. In particular, the presence of magnesium acts on the surface of the metallic implant, in particular if the latter contains iron, local element formation resulting in activation and thus acceleration of corrosion in the treated area.

In a further preferred embodiment the tribochemical treatment takes place in at least two steps, specifically in a first step tribochemical treatment by means of beam particles which exclusively or at least predominantly comprise the at least one inert hard material, and in a second step following on from the first step tribochemical treatment by means of beam particles which at least partially comprise the at least one salt and/or the at least one compound to from the group containing Mg, MgO and Mg(OH)$_2$ and/or at least one metallic material, in each case where required as reagent in microencapsulation.

Conducting the tribochemical method in two steps results in the advantage where the beam particles introduced in the second step adhere better due to the roughness of the surface created by the first procedural step. A large total quantity of beam particles with an overall greater weight of beam particles can be separated out than in a method without the first step due to the larger surface in the second step achieved by surface fracturing. The particles beamed in the second step preferably have a smaller diameter than the particles beamed in the first step. The advantage here is that the particles used in the second step can penetrate deeply into the surface structure generated in the first step (see also FIG. 1).

The at least two-stage method is therefore also an advantage, because with a further coating of the surface (described hereinbelow) by means of a pharmaceutically active substance substantial fracturing of the surface achieved by the first procedural step is likewise advantageous. The surface content increased substantially by fracturing, which can be up to five times greater than the surface content ascertainable geometrically due to the implant dimensions, causes a clear increase in the capacity for storing pharmaceutically active substances and thus prolonging the period over which these can be released.

In a further embodiment the beam particles used for tribochemical treatment have at least one phosphate compound, preferably a zinc phosphate compound.

This embodiment achieves an extension of degradation, that is, a lifetime extension of the implant in particular when using a mixture of titanium oxide particles (for example P25 by Degussa) and zinc phosphate particles of varying granulation. A layer of beam particles several 10 nanometers thick forms on the implant body, depending on the procedural parameters. Even with adhesion of only a minimal portion of these particles to the material of the implant body an effect inhibiting corrosion occurs, resulting in a lifetime extension of the implant under the conditions of the body medium. It is an advantage here that zinc phosphate in the above-mentioned minimal layer density range and titanium oxide independent of layer thickness cause no negative biochemical reactions.

This embodiment of the inventive method is especially interesting for orthopedic implants (endoprostheses) and closes the previous gap between an implant ("normally") degradable over many months and the non-degradable implants of materials such as 316L, CoCr, titanium alloys etc.

In another highly advantageous embodiment at least some of the beam particles have a micro-encapsulated reagent, wherein microencapsulation preferably has at least one thermo- and/or photo-unstable and/or mechanically unstable predetermined breaking point.

This embodiment is based on using micro-encapsulated beam particles which are accelerated in the direction of the surface of the implant, wherein acceleration takes place in the direction of the implant surface at different pressures, variable angles and distances. The thermo- and/or photo-unstable wall of the instances of microencapsulation are preferably configured by means of azo functions (—N=N—) or dioxy functions (—O—O—).

Mechanical predetermined breaking points in microencapsulation based on wall thickness differences can also be provided, made by a corresponding geometric surface structure of microencapsulation. Here the thinnest areas of microencapsulation constitute the mechanical predetermined breaking points which break on the implant surface on impact of the micro-encapsulated beam particles and cause the desired release of the chemically active reagent arranged inside the microencapsulation. The microencapsulation, comprising for example a polymer material, is first deformed solidly and plastically when the micro-encapsulated beam particles impact the surface of the implant. The majority of the microencapsulation is destroyed, the sleeve bursts in those regions with the least wall thickness and the chemical reagent arranged in the interior is released. That part of the micro-encapsulated beam particles, that is parts of the microencapsulation (sleeve) and/or at least part of the reagent contained inside, not immediately bouncing off or reflected by the implant surface, adheres to the surface of the implant. This sets off a chemical reaction, to which the material of the implant, the material of the microencapsulation and the released chemical reagent are added. Increased humidity and increased temperature in the treatment chamber accelerate the corrosion procedure initiated by the chemical reaction.

Each of the abovementioned beam particle materials can be used in principle as reagent contained in the microencapsulation. A biodegradable polymer and an active reagent can be used alternatively or additionally as microencapsulation material, resulting in degradation effects on the implant surface, which would not have materialized under the effect of the individual components. For example, a reaction between a polymer such as PLA as microencapsulation material and NaCl, MgCl or iron(III)-chloride-hexahydrate or manganese (II)-chloride as reagent thus causes a strong shift of the pH value on the surface of the implant into the acidic range. The severe corrosion hereby incipient especially in the moist medium results in the development of iron oxyhydroxides. These adhere only weakly to the material of the implant and are subverted during the course of ongoing corrosion by bodily fluids (plasma, blood) containing chloride ions, causing substantial roughening of the surface of the implant such that the surface content of the implant enlarges and corrosion advances in depth. These effects already set in after very short periods of a few seconds to minutes and can further reinforce corrosion of the implant material generated by the beam particles newly introduced during ongoing tribochemical surface treatment. Following tribochemical surface treatment by means of micro-encapsulated beam particles overall this results in a roughened surface which is highly suited to further surface treatment (e.g. final immersion in biodegradable polymer) due to its roughness and surface activity.

In terms of using micro-encapsulated beam particles it is also preferred to produce more compounds on the surface of the implant via chemical modification of microencapsulation and reagent. Where phosphorous compounds (preferably di-, poly- or cyclophosphates) are used as reagent, iron phosphates can be produced on the implant surface. In this way tailored degradation times can be set depending on the concrete composition of the implant surface and the proportions of iron oxihydroxides and iron phosphates contained therein. The latter are between approximately six and twelve months.

Metals, whereof the compounds or alloys are encapsulated, can in particular also be used as micro-encapsulated reagents.

Metals, which differ substantially in their position in the electrochemical series from that of the implant material, can adhere on impact with the implant surface. At those places where the metals adhere the consequence is formation of local elements accelerating corrosion. This is favored by high humidity of the environment.

In another embodiment polymer-sheathed zinc phosphate (tertiary zinc iron (II)-phosphate), $Zn_2Fe(PO_4)_2*4H_2O$ and/or hopeite crystals (tertiary zinc phosphate), $Zn_3(PO_4)_2*4H_2O$ can be applied to the surface of the implant following a corrosion process, in particular following use of microencapsulated beam particles. The surface of the implant is preferably previously dried. Depending on the procedural parameters employed, applying these materials to the surface of the implant causes a temporary halt to the corrosion procedure and also enables long-term storage of the tribochemically treated implant under non-inert conditions.

In another preferred embodiment following tribochemical treatment outsourcing of the tribochemically treated implant body occurs at increased humidity, in particular at humidity greater than 80%, and/or at increased temperature, in particular at a temperature of more than 50° C.

Particularly accelerated corrosion of the body surface is achieved by the specified subsequent processing of the implant body, in particular following tribochemical treatment by bombardment with beam particles containing at least one salt. Said subsequent processing, in particular outsourcing at increased humidity, causes the occurrence of quite specific, locally qualitative different hole corrosion effects.

In this embodiment of the inventive method the implant is also removed from the chamber preferably after a variable, though preset, effective time at increased humidity and/or increased temperature (for example after 24 hours to 72 hours at relative humidity of 80% to 98% at a temperature of approximately 20° C. to 90° C.) and where required rinsed thoroughly with distilled water. To prevent further corrosion processes proceeding uncontrolled the implant is then provided with a standard corrosion inhibitor, for example magnesium stearate and/or parylene (see below), and dry-stored. Alternatively, the treated implant can also be stored in inert gas. The corrosion inhibitor can also be dispensed with if required when storage is under inert gas.

It is also an advantage if following tribochemical treatment and where required following outsourcing of the tribochemically treated implant body at high humidity and/or high temperature, further coating of the tribochemically treated implant body at least on part of its tribochemically treated surface takes place with magnesium stearate and/or parylene and/or a pharmaceutically active substance.

A "pharmaceutically active substance" (or therapeutically active or effective substance) is understood in terms of the invention as a plant, animal or synthetic material (drug) or a hormone, employed in an appropriate dose as therapeutic agent to influence states or functions of the body, as a substitute for substances produced naturally by the human or animal body, such as insulin, and to eliminate or neutralize illness exciters, tumors, cancer cells or foreign bodies. Releasing the substance in the environment of the implant has a positive effect on the healing course or counters pathological changes in the tissue as a result of surgical intervention or serves to neutralize sick cells in oncology.

Such pharmaceutically active substances present for example an anti-inflammatory and/or antiproliferative and/or spasmolytic effect, by which restenoses, inflammation or (vessel) spasms can for example be prevented. Such substances can for example comprise one or more substances of the active ingredient group of calcium channel blockers, lipid regulators (such as for example fibrates), immunosuppressors, calcineurin inhibitors (such as for example tacrolimus), antiphlogistics (such as for example cortisone or diclofenac), anti-inflammatories (such as for example imidazols), anti-allergenics, oligonucleotides (such as for example dODN), estrogens (such as for example genistein), endothelium agents (such as for example fibrin), steroids, proteins, hormones, insulins, cytostatics, peptides, vasodilators (such as for example sartans) and antiproliferatively effective substances, taxols or taxans, here preferably paclitaxel or sirolimus.

Coating the tribochemically treated surface of the implant using parylene and/or magnesium stearate is an advantage, as the surface properties, for example corrosion advance already completed during the subsequent processing step, are 'frozen' by the overlying coating. The surface properties, which if needed otherwise depend on the storage or transport duration of the implant until introduced to the organism to be treated, and thus also the degradation duration can be adjusted hereby reproducibly and defined. This effect is based on the effect as diffusion barrier relative to permeation of water molecules and chloride ions.

In the case of coating with parylene the high gap mobility of parylene has an advantageous effect, so that deep penetration of the fracturing produced by tribochemical treatment also occurs down to the very bottom of the fracturing. In connection with subjacent tribochemically created surface the permeation properties for water characteristic for parylene, in particular parylene N, solutions containing chloride and hydrogen provide a particularly well controlled degradation performance of the implant. This is also distinguished by slow corrosion advance uniform over the implant cross-section. The parylene-layer also makes an additional contribution to preventing or hindering the advancing of tearing under mechanical load and prevents partial layer peeling.

Parylene is the designation for fully linear, partly crystalline, non-cross-linked aromatic polymers. Different polymers have different properties and can be divided into four basic types, specifically parylene C, parylene D, parylene N and parylene F. Parylene N is preferably used for more coating following tribochemical treatment.

An implant, which is distinguished by freedom from defect of the body surface via subsequent to sealing, can be manufactured by means of the inventive method by coating with magnesium stearate. Local imperfections and/or pores and fracturing present on the body surface of the implant are protected effectively from contact with corrosively acting bodily fluids. The effect of the hydrophobic surface property and the minimal crystal water content of the magnesium stearate, which is also created by a drying stage preferably carried out following application of the magnesium stearate coating, is extremely minimal diffusion of water to the basic material of the implant body during subsequent storage and transport of the implant. The detaching of particles with minimal binding inclination from the surface of the implant body is likewise prevented during dilation. These particles remain in the tender, highly flexible magnesium stearate layer, resulting in increased hemo- or biocompatibility.

An advantageous effect of the magnesium stearate coating of the implant body is that the friction coefficient of the implant drops. The consequence of this is that minimal forces have to be expended in moving a stent as implant in a catheter, for example. Also, crimping and later release of the implant at the site to be treated are simplified. The effect of slight friction during crimping is that scratching of the coated stent surface is minimized or at best prevented.

In a preferred embodiment of the inventive method the magnesium stearate coating is applied by means of immersion in a solution, wherein the solution contains magnesium stearate and a solvent, preferably acetone and/or isopropanol, and preferably has a temperature between approximately 10° C. and the respective boiling point of the solvent. Alternatively, the magnesium stearate layer can also be applied such that said solution containing magnesium stearate is sprayed onto the body of the implant (spray coating). In the process, the part is suspended on a thin wire in a cabinet and sprayed on all sides by means of a rotating plate (batch holder).

In a preferred embodiment the effectiveness of the immersion process can be raised by applying pressure, less than ambient pressure, preferably less than approximately 90% of ambient pressure, that is, of air pressure at the site where the immersion process is performed. The resulting degassing effect leads to rapid filling of the filigree surface structure of the to implant with magnesium stearate. After a dwell time of a few minutes in the solution, preferably at least approximately 2 minutes, the implant body coated with magnesium stearate is removed from the immersion bath and dried in the drying kiln at a temperature above room temperature, preferably greater than approximately 30° C. Here it is particularly preferred if the drying temperature is as low as possible, that is, between approximately 40° C. and approximately 70° C., since this gives slow release/evaporation of the at least one solvent, producing a pore-free layer containing magnesium stearate.

An above-described polymer covering layer of a tribochemically treated implant has a tensile peel strength greater by a factor of 2 than in an implant not treated tribochemically.

In another embodiment the average particle size of the beam particles is approximately 5 nm to approximately 20 μm, preferably approximately 1 μM to approximately 3 μm. This particle size has proven particularly advantageous in typical geometries of implants, in particular stents (ridge widths ca. 100 μm). In tribochemical treatment with maximum-sized particles of a few μm, no plastic deformation of the implant structure occurs. In more robust orthopedic implants beam particles with a size of up to 20 μm can be used. The particle size is measured by the above-mentioned method.

In a preferred embodiment the body of the implant preferably contains a degradable metallic material, preferably predominantly iron, in particular more than 90% by weight iron, particularly preferably at least 99% by weight iron, in particular in an alloy. Manganese, zinc and/or wolfram can be used alternatively or additionally as further metallic materials.

Because they can be manufactured cost-effectively, these implants are particularly preferred in use for treatment of illnesses of the human or animal organism. In particular, in implants containing iron the tribochemical surface treatment, preferably performed in a pressure range between 0.5 bar and 5 bar, results in reduced degradation duration, effectively closing a gap between the degradable and non-degradable alloys for implants.

Tribochemical treatments can be carried out with known radiation installations easily and cost-effectively. To guarantee tribochemical treatment of the entire surface of an implant with an opening or an enclosed cavity, preferably a stent, radiation mechanisms which use a mandrel as jet nozzle are used in the inventive method. In the region of its jet nozzles such a mandrel has a diameter which is clearly smaller than the diameter of the opening or of the cavity of the implant into which the mandrel is inserted for irradiation. By way of example, in the region of its nozzles the mandrel of a radiation mechanism for irradiating the inner surface of a stent has an external diameter which is clearly smaller than the inner diameter of the stent.

Alternatively, tribochemical treatment can also take place in alternating electrical fields. This applies whenever electrically conductive particles (metals or hard material particles such as for example TiN) are employed as beam particles. At the same time, the mandrel functioning as jet nozzle and the perforated sleeve enclosing the endoprosthesis and likewise acting as particle reservoir is connected to an alternating voltage source. The implant acts as a counterpole. With the tribochemical process starting by closing the electrical contact the particles lying opposite the endoprosthesis on potential are accelerated out of the mandrel and the sleeve in the direction of the endoprosthesis.

Different acceleration effects, which in turn lead to kinetic energy of the particles of varying intensity, arise from the adjustable difference in potential. The roughness of the body surface and the depth effect with respect to increasing the dislocation density can thus be adjusted.

The above problem is further solved by an implant obtainable through an abovedescribed inventive method. Such an implant has the advantages specified above in connection with the inventive manufacturing method. The surface morphologies and surface compositions resulting from tribochemical treatment are characteristic for this treatment and are evident on the finished implant.

In a preferred embodiment of the inventive implant the latter has beam particles at least on part of the surface of the implant body or at a slight depth in the surface of the implant body.

In particular, following tribochemical treatment with inert hard particles the inventive substrate presents a fissured surface structure, wherein the fissured structure has the above-described properties and advantages.

It is likewise preferred if the surface of the implant body has at least partially a coating which contains magnesium stearate and/or parylene and/or a pharmaceutically active substance. Here, preferred layer densities of the parylene coating are between approximately 0.5 and approximately 2.0 μm.

The preferred thickness of the magnesium stearate coating is approximately 0.5 μm to approximately 2.0 μm, preferably approximately 0.7 μm to approximately 1.0 μm. The concentration of the magnesium stearate in the other coating is approximately between 80% by weight and 100% by weight.

To a large extent and according to the respective application of the implant the degradation time of the implant can be varied and defined by tribochemical treatment and subsequent coating by means of magnesium stearate and/or parylene.

The inventive method or the inventive implant is explained hereinbelow in examples by way of examples figures. All described and/or graphically illustrated characteristics form the subject matter of the invention, independently of its abstract in the patent claims or any other claims related thereto.

DESCRIPTION OF THE DRAWINGS

The invention is described based on the attached drawings.

DETAILED DESCRIPTION OF THE INVENTION

Figure 1:
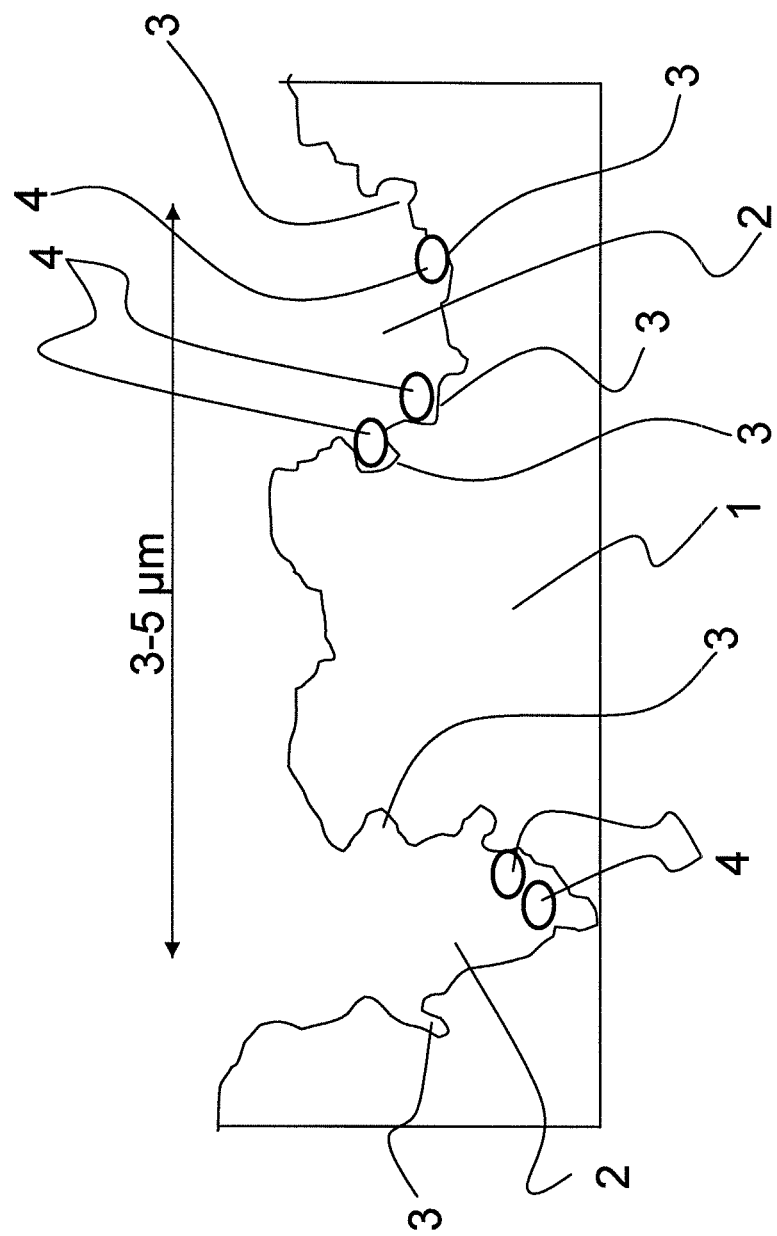
FIG. 1 schematically illustrates a cross-section of a roughened surface of an inventive implant following 24 hours storage in a moist atmosphere (80% humidity) at 50° C.

FIG. 1 shows a cross-section through the near-surface region of a tribochemically treated implant 1. The surface has structures in the form of micro-roughenings 2 which result from bombardment by large hard-material beam particles and/or beam particles of higher kinetic energy. The depth of such micro-roughenings is a few micrometers. The magnitude ratios are depicted by the arrow shown at the top of FIG. 1, symbolizing a dimension of 3 μm to 5 μm. High kinetic energy can be achieved both by a large mass of beam particles and by high beam pressure or high speed of the beam particles. As already explained, kinetic energy can be varied by the electrical parameters of the alternating fields.

Submicro-roughenings 3 contained in the surface profile (surface structure), clearly smaller than the micro-roughenings 2, originate from use of smaller beam particles containing salt, which adhere to the surface as salt particles 4 and have an immediate corroding effect under moist environmental conditions. With the development of submicro-roughenings 3 reactions favoring corrosion, initiated by the beaming of micro-encapsulated beam particles with predetermined breaking points in microencapsulation, can also be involved. The submicro-roughenings have a diameter of approximately 10 nm to approximately 200 nm.

Figure 2:
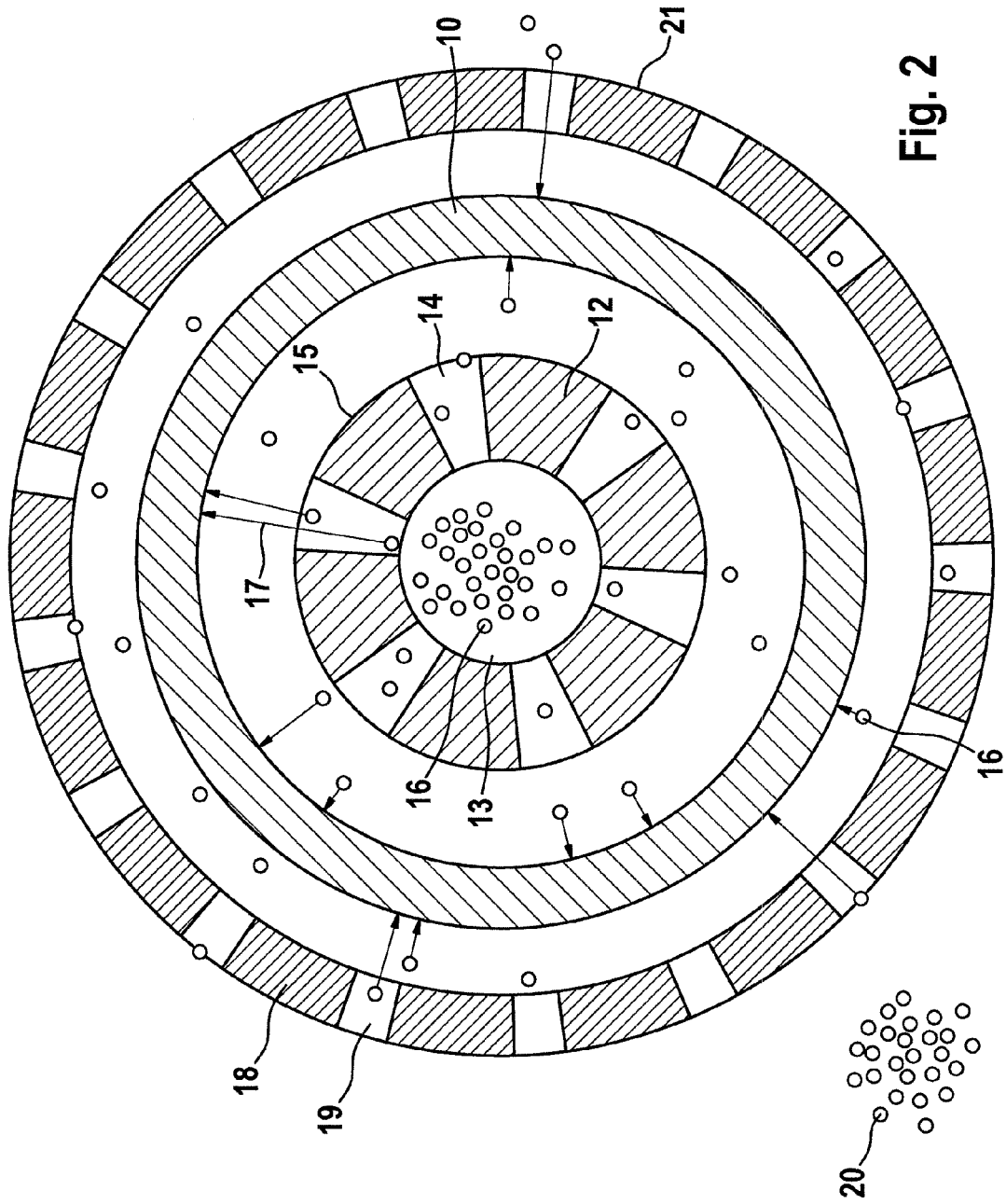
FIG. 2 schematically illustrates a cross-section of an electrically supported tribochemical coating chamber.

FIG. 2 shows a cross-section through an installation, by means of which tribochemical irradiation can take place. A stent 10, which has a hollow cylindrical shape and is thus represented in cross-section as a circular ring, is tribochemically treated by the installation for example. Arranged in the inner volume of the stent 10 is a mandrel 12 with a concentric opening 13 provided on the mandrel tip and radial openings 14. Further, the stent 10 is surrounded by a sleeve 18 with radial openings 19. Provided in the mandrel 12 and outside the sleeve 18 is a reservoir of beam particles 16, which are accelerated from the mandrel 12 to stent 10 or from the sleeve 18 to the surface of the stent 10. The beam particles 16 move in through the corresponding openings 14 or 19. The direction of movement of the beam particles 16 is indicated for some beam particles by an arrow 17. The beam particle reservoir of the sleeve 18 is illustrated in FIG. 2 only schematically and provided with reference numeral 20. An increase in kinetic energy of the beam particles can occur by applying an electrical field. For this, on the one hand the stent 10 and on the other hand the mandrel 12 or the sleeve 18 lie on a different electrical potential. The mandrel 12 has poling 15 and the sleeve 18 has poling 21 to generate the difference in potential.

The invention will be explained in more detail hereinafter based on the exemplary embodiments.

Example 1

Tribochemical Treatment of an Implant by Means of Hard-Material Beam Particles

This example concerns tribochemical treatment of an implant by means of hard particles. The hard particles comprise a mix of microscale beam particles of TiC, WC and TiCN. The average grain size of the beam particles is 4 μm at a spread of +/−1 μm. Tribochemical treatment takes place in a tribochemical installation. The beam particles are beamed by means of the radiation installation shown in FIG. 2 at the same time onto the inside and the outside of the implant by means of compressed air at 3 to 4 bar pressure. The process evolves over a period of 5 min. This results in elastic and plastic deformation effects of the surface of the implant, the body of which is composed of pure iron or an iron-based alloy with alloy constituents such as Mn, Si, Pd, Pt and/or other constituents. The plastic deformation portion leaves behind the surface morphology illustrated in FIG. 1 (without the submicro-roughenings originating from subsequent salts).

Micro-hardness examinations of such a treated implant of pure iron have shown that a micro-hardness increased relative to the structural component interior by up to 150 HV 0.1 to a rough depth of 10 μm is present in the near-surface volume region deformed plastically by the beam particles.

Example 2

Tribochemical Treatment of an Implant by Means of Beam Particles from Salts

Salts comprise a mixture of in each case 50% mass NaCl and $MgCl_2$. The beam particles have a particle size varying between 200 nm and 20 μm and are beamed onto the surface already preliminarily damaged by the hard-material particles in accordance with the process described in embodiment 1. The process is carried out in a tribochemical treatment installation in FIG. 2 illustrated in section at pressures specified in Example 1. To avoid clumping of the hygroscopic salt mixture, the latter must be stored dry prior to and during the tribochemical treatment process.

In addition to supply by compressed air the sleeve and the mandrel can be supplied by an electric potential different to the latter relative to the implant, resulting in electric charging of the salt particles. Compared to the currentless treatment variant the result of this is increased acceleration of the particles in the direction of the implant surface. Increased temporary adhesion of the salts in the micro-roughenings and the resulting stronger characteristic of submicro-roughenings are the consequence.

The chloride beam particles disassemble on impacting the surface of the implant into many small fragments which are reflected back partially by the surface and ricochet on the latter.

The fragments of the beam particles adhering to the surface react in the abovedescribed way with the implant material and produce the submicro-roughenings.

Example 3

Tribochemical Treatment of an Implant by Means of Beam Particles of Mg, MgO and/or $Mg(OH)_2$ The tribochemical treatment parameters for irradiation by means of the beam particles used in this example are identical to the parameters mentioned in embodiment 1. But less plastic deformation and less roughening of the surface of the implant are caused due to the lesser hardness of the beam particles. The mixture ratio of the beam particles is made up of 30% mass Mg (average particle size 10 μm), 30% mass MgO (average particle size 10 μm) and 40% mass $Mg(OH)_2$ with an average particle size of 3.5 μm. This mixture ratio on the one hand diminishes the danger of auto-ignition, and on the other hand the affect of partial adhesion of the metallic Mg on the implant surface, which contains iron for example, is strong local element formation. The conductivity of the magnesium here also offers the possibility of particle acceleration through applying electrical alternating fields. At the same time, the Mg beam particles are almost exclusively accelerated and irradiated onto the endoprosthesis surface. Tribochemically created multi-layers can be generated through reciprocal operation of the tribochemical treatment installation (with and without electrical alternating field).

Example 4

Tribochemical Treatment of an Implant by Means of Titanium Oxide or a Mixture of Titanium Oxide and Zinc Phosphate Procedural parameters and particle sizes as in Example 1.

For application as beam particles in the inventive method it is not essential in which modification (rutile, anatas or brookite) the titanium oxide is present. The alternating electrical field support for acceleration of beam particles cannot be applied, since the particles are not conductive. Due to the minimal hardness of the beam particles only minimal stabilization of the surface and only minimal roughening occurs. Contrary to the other embodiments the adhered particles influence degradation performance in the direction of delayed degradation (for example, lifetime of an iron-based stent is increased to 1.5 times).

Example 5

As Per One of Examples 1 to 4 and Additional Coating by Means of Parylene, Magnesium Stearate and/or Pharmaceutically Active Substances On the basis of all previously mentioned embodiments coating with the above-mentioned materials can be a final treatment step. Coating with parylene C ensues from the gas phase. After ca. a half hour coating time a layer density of ca. 0.5 µm is achieved.

Parylene coating pursues the goal of temporary corrosion protection. The "pre-damaged" surface state is "frozen." So no uncontrolled degradation proceeding autonomously ensues before the endoprosthesis is brought to the application site.

The same goal is pursued with the magnesium stearate coating described hereinbelow. Following execution of embodiments 1 to 4 and subsequent drying the endoprosthesis is suspended on a synthetic thread (for example polyamide) and then immersed in the solution to apply the magnesium stearate. The solution comprises for example 9 parts high-purity acetone or isopropanol and 1 part magnesium stearate. The immersion procedure occurs at room temperature in an evacuatable desiccator, in which a negative pressure of ca. 100 mbar is generated by means of a pump. As a result of this the filigree microporous surface structures originating from the preceding plasmachemical pretreatment or the undercuts and intricately formed structures are effectively freed of residual gas. Complete covering of the stent surface by magnesium stearate can occur as a result in the solution, which also penetrates the surface structures and undercuts. After a dwell time of approximately 3 minutes in the immersion bath the desiccator is ventilated, the implant is removed from the immersion bath and then dried at a temperature of 60° C. in a recirculation cabinet, while suspended on the synthetic thread. The layer density of the resulting magnesium stearate coating is in the vicinity of approximately 0.5 to approximately 10 µm.

The magnesium stearate is isolated very uniformly on the surface contingent on the negative pressure present in the desiccator. A low drying temperature advantageously causes slow release/evaporation of the solvent of the dipping solution, producing a pore-free magnesium stearate layer. If the resulting implant is a stent, the body provided with the first layer and the intermediate layer can then be completed with a catheter and subjected to radiation sterilization.

As for the production of parylene or magnesium stearate coating the fissured surface of the implant can be coated alternatively or additionally with a pharmaceutically active substance. Preferred substances are specified above in the description.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LEGEND

1 implant body
2 micro-roughening
3 sub micro-roughening
4 adhered salt particle
10 stent
12 mandrel
13 opening
14 opening for beam particles 16
15 poling of mandrel
16 beam particles
17 arrow (direction of movement of respective beam particles 16)
18 sleeve
19 opening for beam particles 16
20 beam particles reservoir of sleeve 18
21 poling of sleeve 18

What is claimed is:

1. A method for manufacturing an implant, optionally an intraluminal endoprosthesis, having a body containing metallic material, optionally iron, comprising the following steps:
   i) providing an implant body;
   ii) micro-roughening a surface of the implant body by beaming electrically conductive particles against the implant body, wherein the electrically conductive particles adhere to the micro-roughened surface of the implant body, wherein the electrically conductive particles are selected from the group consisting of TiN, TiC, TiCN, and CuZn;
   iii) tribochemically treating at least part of the micro-roughened surface by beaming granular salt particles against the micro-roughened surface to adhere the salt particles to the micro-roughened surface to initiate corrosion of the implant body under moist environmental conditions, wherein the salt particles are selected from the group consisting of NaCl, CaCl2, MgCl2 and dry-stored MgCl2; and
   v) storing the implant body in an air free environment that temporarily prevents or reduces corrosion of the implant body by the adhered salt particles.

2. The method as claimed in claim 1, wherein the step of tribochemically treating at least part of the micro-roughened surface comprises inserting the implant body into an installation comprising a jet nozzle in the form of a mandrel and sleeve such that the body surrounds the mandrel and the sleeve surrounds the body, and applying an electric field to the installation to accelerate the beam particles from the mandrel and towards the body, wherein the body has a different electric potential than the mandrel or the sleeve.

3. The method as claimed in claim 1, wherein at least part of the implant body is tribochemically treated by beaming particles comprising a micro-encapsulated reagent, wherein the microencapsulation optionally has at least one thermo-, photolabile and/or mechanically labile predetermined breaking point.

4. The method as claimed in claim 1, further comprising the step of applying a coating of magnesium stearate, parylene, a pharmaceutically active substance, zinc phosphates and/or hopeite crystals to at least part of the tribochemically treated surface of the implant body.

5. The method as claimed in claim 1, wherein the average particle size of the beam particles is approximately 5 nm to approximately 20 μm.

6. The method as claimed in claim 1, wherein the body of the implant is predominantly iron, optionally more than 90% by weight, optionally more than 99% by weight, optionally in an alloy.

* * * * *